United States Patent [19]

Winslow, Jr.

[11] 4,351,703
[45] Sep. 28, 1982

[54] CATHODIC PROTECTION MONITORING

[75] Inventor: Joseph D. Winslow, Jr., Houston, Tex.

[73] Assignee: Petrolite Corporation, St. Louis, Mo.

[21] Appl. No.: 947,149

[22] Filed: Sep. 29, 1978

Related U.S. Application Data

[63] Continuation-in-part of Ser. No. 729,312, Oct. 4, 1976, abandoned.

[51] Int. Cl.$^3$ .................. G01N 27/46; C23F 13/00
[52] U.S. Cl. .................................. 204/1 T; 204/147; 204/195 C; 204/196
[58] Field of Search .......... 204/1 C, 147, 148, 195 C, 204/196, 197

[56] References Cited

U.S. PATENT DOCUMENTS

| | | | |
|---|---|---|---|
| 2,943,027 | 6/1960 | Schaschl et al. | 204/1 |
| 3,486,996 | 12/1969 | Annand | 204/195 C |
| 3,634,222 | 1/1972 | Stephens, Jr. | 204/196 |
| 3,649,492 | 3/1972 | Marsh et al. | 204/148 |
| 3,748,247 | 7/1973 | Weisstuch | 204/195 C |
| 3,948,744 | 4/1976 | Cushing | 204/195 C |

Primary Examiner—Aaron Weisstuch
Attorney, Agent, or Firm—Sidney B. Ring; Hyman F. Glass

[57] ABSTRACT

Cathodic protection monitoring of large metallic structures receiving cathodic current from a remote anodic electrode. Exposed to the cathodic current, closely adjacent the metallic structure, is a metallic specimen with a surface area of less than one-tenth of the structure's area. Current flow is induced between the specimen and the structure until their potential difference is substantially zero. Measurement of the induced current flow allows the current density impressed upon the specimen to be determined, and it is substantially identical to the current density impressed upon the structure by the cathodic current. Anodic and cathodic induced current flows are employed for varying the potential of the specimen relative to the structure (as reference) to determine anodic and cathodic reaction rates, unprotected corrosion rate of the structure, and the cathodic current required to protect the structure. The metallic specimen may be partially encased in an insulating covering.

21 Claims, 4 Drawing Figures

CATHODIC PROTECTION MONITORING

This application is a continuation-in-part of application Ser. No. 729,312, filed Oct. 4, 1976, abandoned.

BACKGROUND OF THE INVENTION

1. Field of the Invention

This invention relates to measuring and testing electrochemical processes; and it relates particularly to processes for the evaluation of protection of large metallic structures against corrosion attack.

2. Description of the Prior Art

Large metallic structures located in land or sea regions, such as pipelines, wells, structural supports and the like are subjected to corrosion attack. To minimize this corrosion attack, these structures may be covered with protective materials such as inert wrappings of fiber or cloth, and exterior impervious coatings of bitumen, cement or the like. Unavoidably, some voids remain within the protective coatings during their application, or are created during the installation of the structure within the earth region or thereafter by mechanical injury. The exposed surfaces of the structure are exposed to corrosion.

Many schemes have been envisioned for protecting these structures. For example, galvanic or electrochemical corrosion attack is very much more common than the usual chemical attack envisioned by the presence of a corrodant. In the electrochemical corrosion attack, the structure is at a different potential level than adjacent galvanic material so that a current flow between the two occurs through the earth region even though it is of substantially high specific resistivity. The presence of oxygen or other type of corrosive medium accelerates the effect of the galvanic corrosion attack. Obviously, corrodants also exist in the earth region about the structure.

The primary method of retarding electrolytic corrosion attack is through the use of cathodic protection. In cathodic protection, the structure receives a flow of current from an anodic (anode) electrode spaced remotely in the earth region. The anode may be a metal, such as magnesium, which has a lower half-cell potential than the structure in the earth region. Alternatively, the anode may be inert, such as a carbon mass, and a flow of cathodic current provided from a suitable d.c. power source. In either event, the flow of cathodic current from the metallic structure to the anode is assumed to be of proper magnitude when the structure (steel) is about 0.25 to 0.30 volts negative relative to the earth region immediately surrounding the structure. A more reliable criterion of proper cathodic protection is the current density of the structure in the amount of at least 3 milliamperes per square foot of the structure in contact with the earth region. Under these conditions, the structure may be directly exposed to the earth formation and all of its proportions are protected against corrosion attack.

Many methods and arrangements have been proposed for evaluating the cathodic protection of a metallic structure. Generally, these techniques measure the potential of the structure in the earth region relative to a closely adjacent reference electrode, such as the copper sulfate half-cell. Unfortunately, the non-isotropic characteristics of the earth region prevent a correlation of the potential measurement relative to the required current flow magnitude from the remote anode(s) for the proper cathodic protection of the entire structure. Repeatedly, prior art schemes concerned themselves primarily with corrections for the resistivity of the earth region in the potential measurement between the structure and the reference electrode. These measurement techniques have failed to provide uniformly acceptable results.

The concept of cathodic protection of an "anodic" structure is a very sound approach to corrosion attack abatement. However, the theory and practices of surveying and monitoring such installations have been irrelevant and invalid because of the assumption that a separate "reference" electrode is required to determine proper cathodic current magnitudes. Fundamental electrical analysis of the problem leads to a different concept.

Cathodic protection of any portion of the structure exists when the anodic reaction rate (dissolution of metal ions) has been suppressed to a magnitude consistent with the corrosion allowance/life time criterion but without an excess suppression causing an accelerated cathodic reaction rate adequate to delaminate protective coverings, etc., or embrittle the structure due to excessive hydrogen generation.

The large metallic structure is a low resistance "conductor" surrounded by a more resistive earth region. Therefore, the structure's "potential" is essentially identical in all portions and throughout its extent. This may be illustrated by analogy with a balloon: the internal pressure (potential) is equal at all parts; and the balloon's walls are distorted by variations in externally applied forces which at some points distort the wall outward, and at others, inward. The stresses in the balloon's wall vary considerably in amount and place depending on variation in local external forces. The measure of stress upon the balloon's wall at any particular point must involve the measurement of the differential between the balloon's internal pressure (constant) and the effective pressure (variant) immediately exterior of the balloon at the point of interest. Only the exterior applied pressure can vary in magnitude since the internal pressure is uniform.

In the large metallic structure, the externally applied force (potential) at any point in the adjacent earth region is the result of the structure's electrochemical equilibrium in association with the earth region environment. The earth region surrounding the structure is not homogeneous and therefore, the local external (potential) "forces" vary from point to point. These different externally applied "forces" cause the electrochemical energy exchange between the structure and earth region and produce corrosion by the evolution of hydrogen at areas of low potential and disassociation of metal atoms at areas of higher potential. Obviously, placement of a reference electrode in an area of low potential produces erroneous measurements for areas of high potential, i.e., the problem of prior art measurement schemes.

The structure is protected cathodically upon effectively equalizing the potentials (or forces) on the structure and the surrounding earth region. Cathodic current from a single anode at some distance from the structure probably will not equalize the entire structure. A multiplicity of anodes are required and each anode adjusted in current flow to equalize the potential "pressure" at all points on the structure. This latter arrangement provides a uniform cathodic reaction over the entire surface of the structure. Thus, cathodic protection requires the pressure alteration of the external environment surrounding the structure to provide equalization of electrochemical potential (substantially zero voltage differential).

It is not possible or practical to isolate the structure into a great number of individual parts without affecting the purposes for which it exists, even if all parts could be joined electronically so as to maintain a uniform structure potential. Also, it is not possible to ascertain the external "potential" force adjacent to each or any part of the structure when mechanically or integrally connected. The vast majority of "cathodic protection" practioners and electrochemists simply determine the in situ electrochemical "contact" and induced potentials of a structure by the measurement of the potential difference between the structure and the sancrosanct "reference" electrode(s) placed in the earth region. The existence of a "component" potential which is the result of the external force acting at a distance from the external surface (IR drop) is a substantial component of the measurable potential difference. As a result, this component potential causes serious errors when surveying cathodically protected systems, whether energized or not.

If each elemental part of the structure were disconnected electronically in turn and one by one from the remaining structure, the free part attains equilibrium with its environment, i.e., the rest of the structure. Subsequent measurements of the difference between the "internal" potential of the structure and that of the "electronically" isolated part would be a direct measure of the influence of the external force at a distance on the structure at that location, i.e., the "polarization" potential shift attributable to the anodic electrode as it affects the structure at that locale in the earth region. Upon reconnection of the elemental part to the structure, a measure of the current between that part and the structure could be made by zero resistance ammeter techniques. As a result, the current (density) and the potential shift to zero potential difference could be measured. Also, if the disconnected part is driven through a limited range of potential magnitude with respect to the remaining structure, both positive and negative several hundred millivolts about the open circuit value, the resulting potential/current responses can be utilized to determine (a) anodic reaction rate, (b) cathodic reaction rate, (c) unprotected corrosion rate, (d) protected corrosion rate, and (e) current density available from anodic ground bed.

The present invention provides a method for producing the above results with the same accuracy and facility as if a part of the structure could be electrically disconnected from the remainder of the structure without destroying its useful purposes.

SUMMARY OF THE INVENTION

In accordance with this invention, there is provided a method for the cathodic protection monitoring of a large metallic structure located in an earth region or in a body of water and receiving current from a remote anode electrode. A metallic specimen is positioned closely adjacent to, but not in direct electrical contact with, the structure. The specimen is exposed to the cathodic current and has a known surface area of at least one magnitude less than the structure. A current flow is induced between the specimen and the structure until the potential difference between the specimen and structure is substantially zero. The induced current flow between the specimen and structure is measured. Then, the current density impressed upon the specimen is determined, and this current density is substantially identical to the current density impressed upon exposed like areas of the structure by cathodic current from the remote anode electrode. In preferred embodiments of the method, the inducing current flow is varied anodically and cathodically to create a potential difference between the specimen and structure not in excess of about 1000 millivolts and preferably not in excess of about 400 millivolts, as the unprotected corrosion rate function, in the linear potential region. From the resultant relationship of potential to current, the cathodic and anodic reaction rates and the cathodic protective current can be determined. In one aspect of the invention, the metallic specimen is partially encased in an insulating covering. The structure may be at least partially covered or encased in a protective material, such as bitumen or concrete or other suitable material, including naturally occurring ones.

DESCRIPTION OF SPECIFIC EMBODIMENTS

The method of the present invention is based upon the recognition that the magnitude of the metallic structure with respect to a sample specimen located adjacent thereto is so large that the structure serves as both a reference electrode and an auxiliary electrode so that current may be passed between the specimen and the structure. In this manner, the potential difference between the specimen and the structure can be monitored relative to the magnitudes of induced current flow therebetween, by suitable means such as a zero resistance ammeter, and the same information regarding corrosion protection can be determined as if the specimen was an electrically disconnected part of the structure. For purposes of the present invention, the zero resistance ammeter of the classic type may be employed. However, a variable conductance ammeter, such as shown in U.S. Pat. No. 3,766,042, can be employed or preferably, a more versatile commercial instrument such as the dynamic analyzer shown in U.S. Pat. No. 3,855,101 and marketed under the name Potentiodyne ® Analyzer.

Figure 1:
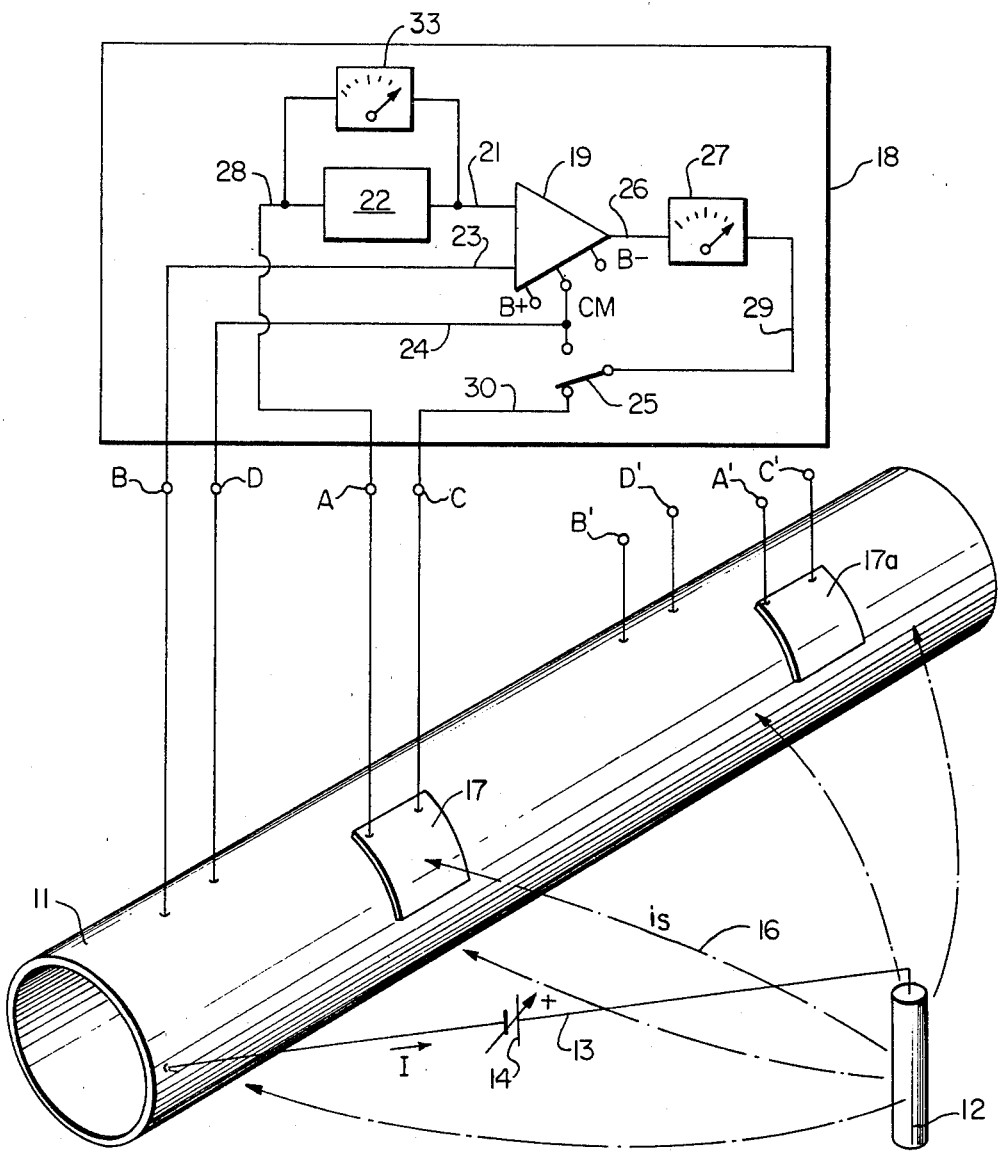
FIG. 1 is an isometric perspective of a pipeline representing a large metallic structure located in an earth region with electronic measurement apparatus for carrying out the method of the present invention.

Referring now to FIG. 1, there is shown a subterranean steel pipeline 11 which represents a large metallic structure located in an earth region, which earth region is omitted from the drawing for purposes of description; however, it is intended that the pipeline 11 is buried within earth formations or submerged within a body of water. The pipeline 11 is shown bare, but may be covered with a coating of protective wrap and treated with a bituminous material for waterproofing purposes, or covered with a coating of concrete or the like when the placement is within a salt water body. The pipeline 11 will usually be protected against electrochemical corrosion through the use of some type of cathodic protection system. For example, the pipeline 11 is protected by a remote anode electrode 12 which is placed within the earth region a selected distance from the pipeline 11. The anode electrode 12 can be of the sacrificial variety, such as a magnesium body, wherein it suffers an anodic reaction within a ground bed to produce a current flow I through an interconnecting conductor 13 so that cathodic protection is provided to the pipeline 11. Alternatively, the anode electrode 12 is shown to be an inert electrode, such as a carbon body, and the cathodic current I is provided by suitable d.c. source 14. As is general practice, a plurality of anode electrodes 12 and conductors 13 are placed along the pipeline 11 to affect a preselected magnitude and distribution of cathodic protective currents.

The return path 16 for the cathodic current I is through the earth region from the anode electrode 12 to the pipeline 11, and these currents are indicated by the reference $i_s$. As is apparent, the return current paths 16 are distributed about the extended surface of a pipeline 11 and depend upon the characteristics of the earth region and the surface condition of the pipeline 11. For example, the return currents $i_s$ might be segregated to a specific locality such as provided by a holiday within the protective coating surrounding the pipeline 11. However, the currents $i_s$ could also be distributed uniformly along a concrete covered pipeline.

In accordance with this invention, a specimen 17, preferably of a like metallic material to the pipeline 11, is placed closely adjacent to, but not in direct electrical contact with the pipeline. The specimen 17 may be held in place with respect to pipeline 11 by electrochemically non-interactive means, such as by epoxy adhesives, or plastic bands, but actual attachment to the pipeline is not required.

The pipeline 11 is a structure of relatively great magnitude compared to the specimen 17. In this regard, the specimen 17 can be considered in relative potential only in that represented by the pipeline 11. Comparison to the prior art usage of reference electrodes spaced adjacent to the pipeline 11 shows clearly that the use of an artificial reference electrode(s) create(s) errors of great magnitude in comparison with specimens referenced exclusively to the pipeline 11 in accordance with the present method.

Ideally, the material of the specimen 17 should be identical with that of the pipeline 11. However, it is recognized that absolute identity of materials, even in the same mill run, is metallurgically impossible. Under some circumstances near identical materials may be used to advantage, for example: (a) when so called "identical" material is unavailable; (b) when a specimen material of near identity, but scientifically significant differences, itself requires testing in the environment; (c) and when a dissimilar material is contemplated to be adjacent or connected to the structure and that material in conjunction with the common internal potential of the main structure by way of mechanical and/or lattice bonding will require common source anodic protection. The term, "like metallic material," is intended to cover "identical" and near identical material.

Since the specimen 17 is not in direct electrical contact with the pipeline 11, a medium of some specific resistivity resides between the specimen 17 and the pipeline 11. This medium usually is a part of the earth region. Importantly, the specimen should have a surface area at least one magnitude less than the surface area of the pipeline 11 exposed to the cathodic current provided by the anode electrode 12. In one example, the specimen 17 has a planar form with an exposed surface area of about a square foot for the pipeline 11 having diameters of 6 inches or more and lengths of several thousand feet. For extended lengths of the pipeline 11, additional specimens (17a) are spaced apart along the surface of the pipeline 11.

It is evident that the specimen 17 receives in proportion to its surface area a portion of the return current $i_s$ along path 16. In addition, the same current density impinged upon the specimen 17 is applied to a like surface area of the pipeline 11.

Under conditions where cathodic current flow is present between the anode electrode 12 and the pipeline 11, a galvanic or freely corroding potential $V_{oc}$ exists between the specimen 17 and the pipeline 11. More particularly, the potential $V_{oc}$ is truly reflective of the condition as if the equal area portion of the pipeline 11 were disconnected from the remainder and was at equilibrium with the surrounding earth region. Thus, the specimen 17 provides an isolated part in equal area of the pipeline 11 under conditions that represent an equilibrium potential $V_{oc}$ between that isolated portion (specimen 17) and the remainder of the pipeline 11 within the earth region. If the potential $V_{oc}$ of all the specimens 17, 17a, etc., and the pipeline 11 are identical, all parts of the pipeline 11 are cathodically protected by identical cathodic current and anode electrode(s) 12 arrangements. Where the potential $V_{oc}$ is not the same for all specimens, then different portions of the pipeline 11 require different cathodic current flow magnitudes for cathodic protection.

Box 18 shows electronic circuitry which may be employed for monitoring purposes. However, as indicated above, a zero resistance ammeter, a variable conductance ammeter as shown in U.S. Pat. No. 3,766,042, or an infinite conductance potentiostat such as disclosed in U.S. Pat. No. 3,855,101, may be substituted. With respect to box 18, the four terminal cell connections to the instrument are represented by letters B, D, A and C. The circuitry includes an operational amplifier 19 having a first input 21 containing a variable voltage source 22 in series to conductor 28 and terminal A. The second input 23 of the amplifier 19 is connected directly to the terminal B. The circuit common terminal 24 of the amplifier is the current return terminal D of the circuitry. The output 26 of the amplifier 19 connects through a suitable ammeter 27 to terminal C through conductor 29, switch 25 and conductor 30. A voltmeter 33 is connected in parallel across voltage source 22 between conductors 21 and 28.

Measurement of the potential $V_{oc}$ of the specimen 17 relative to the pipeline 11 is obtained through the connection of terminal A to the specimen 17 and terminal B to the pipeline. The variable voltage source 22 is adjusted such that zero current flow is indicated in ammeter 27 with the switch 25 in its upper position. As a result, the potential $V_{oc}$ between the specimen 17 and the pipeline 11 is identical in magnitude, and of reverse polarity, to that of voltage source 22, measured between points 21 and 28 by voltmeter 33. The amplifier 19, with the usual connections to a suitable power source represented as B+ and B−, produces a current through the ammeter 27 representative of the difference in potential $V_{oc}$ of the specimen 17 relative to pipeline 11 and the potential of source 22. The voltage source 22 is adjusted to the value $V_{oc}$, the current through ammeter 27 thereby becoming zero. For example, the open circuit voltage $V_{oc}$ between the specimen 17 and the pipeline 11 may be 300 millivolts.

After the open circuit potential $V_{oc}$ is determined, the switch 25 is placed into its lower position so that cathodic protection current can flow through terminal C and the return current $i_s$ passes through the terminal D. The specimen 17 now has an induced potential developed relative to the pipeline 11. The variable voltage source 22 is adjusted to zero so that the potential between the specimen 17 and the pipeline 11 is at substantially zero. Stated in another manner, the specimen 17 and the pipeline 11 are at the same potential within the earth region. Under these circumstances, the specimen 17 has been brought electrically into an identical condition as if the pipeline 11 had a segment physically separated from it as the specimen 17 but electrically connected thereto for the receipt of the returning current $i_s$ in the current paths 16. The amplifier 19 produces a current through terminals C and D, which current is representative of the cathodic protection current impressed on a like segment of pipeline 11. The current flow from the amplifier 19 is the readout in the ammeter 27 of the identical return current $i_s$ impinged upon that known area of the specimen 17.

The current $i_s$ impinged upon the specimen 17 for a known area provides the current density (amperes/square meter) resulting from the operation of the anode electrode 12 in providing cathodic protection to the pipeline 11. Since the specimen 17 and the pipeline 11 are at identical potential, like elements of pipeline 11 must receive the same return current $i_s$ as has the specimen 17 and must have the same current density. The use of a plurality of specimens 17, such as 17a, etc., along the pipeline 11 permits the determination of the current density imposed upon these spaced apart portions.

Figure 2:
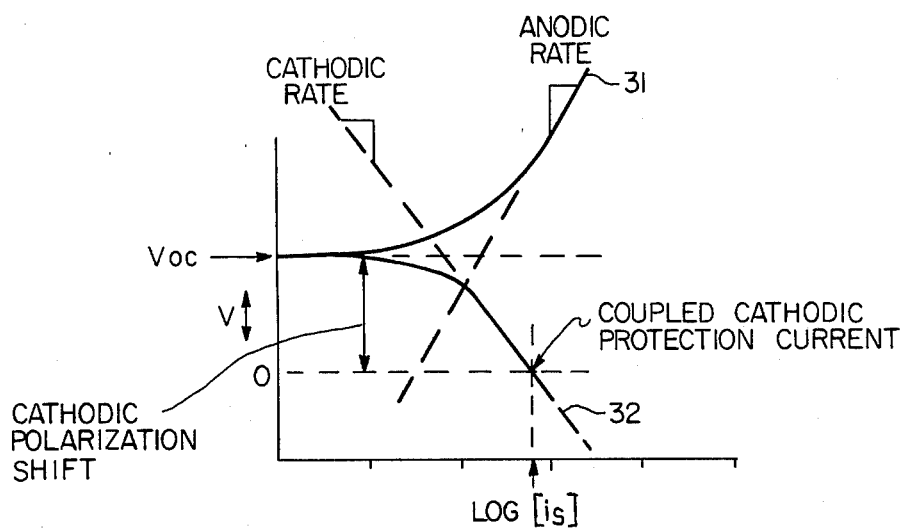
FIG. 2 is a graphic representation of the data obtained with the electronic circuitry shown in FIG. 1.

In addition, this arrangement is employed to determine several additional informations regarding the corrosion protection of the pipeline 11 by cathodic currents. Referring to FIG. 2, the circuitry of FIG. 1 is used through adjustment of the variable voltage source 22 so that the specimen 17 is varied potentialwise relative to the pipeline 11. For example, the variable voltage source 22 is adjusted so that the specimen 17 is moved voltagewise from the potential $V_{oc}$ to a second potential to induce anodic current flows from the specimen 17. The shift from the first to the second potential of the specimen 17 should be of a magnitude sufficient to determine anodic reaction rate as is graphically displayed by the curve 31. The curve 31 represents the anodic corrosion phenomena occurring about the pipeline 11. The Tafel slope of the curve 31 represented by the voltage along the ordinate and the log of the return current $i_s$ along the abscissa is the anodic reaction rate of the curve 31. In a like manner, the voltage of the specimen 17 through adjustment of the variable voltage source 22 is moved from the potential $V_{oc}$ to a second potential to induce cathodic current flow to specimen 17. The differences in potential between the initial potential and the second potential of the specimen 17 should be of sufficient magnitude to determine the cathodic current reaction rate from the curve 32. The Tafel slope of the curve 32 between the voltage differential and the log of the return current $i_s$ represents the cathodic reaction rate about the pipeline 11. When the voltage shift of the specimen 17 is in the direction to induce cathodic current flow, the voltage differential $V_o$ between the specimen 17 and the pipeline 11 becomes zero. At this condition, the abscissa intercept of the curve 32 at potential differential $V_o$ is the cathodic protective current (or coupled cathodic protection current) represented by the logarithm of return current $i_s$. At this current $i_s$ magnitude, the pipeline 11 is properly protected by that exact magnitude of current flow I from the anode electrode 12. The measurement procedure can be repeated for each additional specimen 17a by moving the electronic circuitry within the box 18 to the other specimen 17a, and so forth.

It will be appreciated that the difference in potential between the specimen 17 and the pipeline 11 of the open circuit potential $V_{oc}$ and zero potential difference $V_o$ at the coupled cathodic protective current, provides a measure of the cathodic polarization and protection provided by the remote anode electrode 12 to the specimen 17, and conjunctively, to the pipeline 11.

With practice of the foregoing method, the proper cathodic protective current for the pipeline 11 can be determined throughout its extent. As a result, sufficient cathodic protective current can be arranged for any given segment of the pipeline 11 and at no point along its extent is there an overabundance of cathodic current to produce hot spots, hydrogen embrittlement and like undesired reactions. Thus, the method of the present invention provides a current-conductance profile of the pipeline 11 through a plurality of specimen(s) 17 at various points of interest. Since the pipeline 11 is both the reference and auxiliary electrodes of the corrosion measurement system, all perturbations based upon use of external reference electrodes, such as the copper-copper sulfate variety, and variations in ground bed resistances are avoided.

In the above described embodiment, as illustrated in FIG. 1, two leads from the specimen 17 are employed leading to terminals A and C, since a four terminal instrument is used. However, a total of two leads, one from the specimen and one from the structure would suffice.

It will be readily appreciated by those skilled in the art that if the variable conductance ammeter of U.S. Pat. No. 3,766,042 is substituted for the circuitry of box 18, terminals R, A, T and T' may be used for terminals A, C, B and D, respectively, of the present invention. It will likewise be appreciated that if the Potentiodyne Analyzer of U.S. Pat. No. 3,855,101 is employed, terminals A, B, C and D shown in FIG. 1 thereof will correspond to like designated terminals of the present invention.

Figure 3:
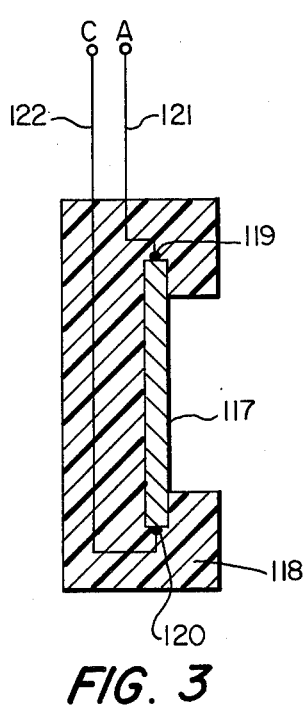
FIG. 3 is a sectional representation of a metallic specimen partially encased in an insulating cover.

In one aspect of the present invention, illustrated by FIG. 3, the metallic specimen designated here as 117 is partially encased in an insulating covering 118. Such insulating covering may be of any suitable electrochemically non-interactive substance, such as epoxy plastics, laquer, rubber, Teflon, etc. Preferably the insulating covering is bonded to the specimen at unexposed surfaces. Terminals A and C are connected via lead wires 121 and 122, respectively, to the encased portion of the specimen 117, the connections as shown being at points 119 and 120, respectively, at opposite ends of the specimen. Instead of being positioned at such opposite ends, the connections may be made at any other points within the encased portion of specimen 117 except in direct alignment through the specimen with the exposed test area, i.e., lead wires 121 and 122 should preferably not be adjacent to each other within the encased portion of the specimen, although at the low current deviation of normal expected use, lead placement is relatively unimportant. It is advantageous to minimize the ratio of edge of exposed specimen surface to exposed specimen area.

Figure 4:
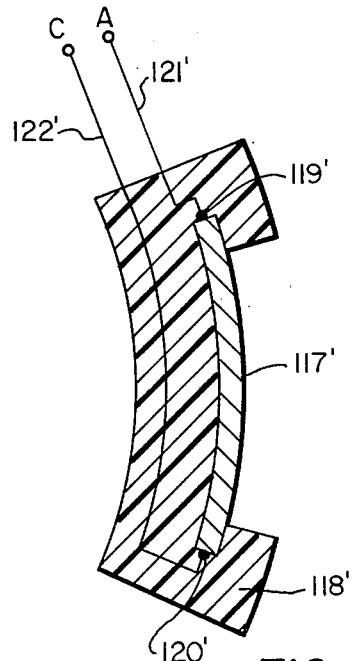
FIG. 4 is a sectional representation of another embodiment of a metallic specimen partially encased in an insulating cover, suitable for use in the system specifically illustrated in FIG. 1.

In FIG. 3, the specimen 117 is shown as uncurved, a shape suitable for use in connection with a structure having a non-curved surface. FIG. 4 illustrates a modification of FIG. 3, wherein the specimen 117' is curved so that it may be conveniently employed in connection with pipeline 11 or other structure having a similar curved surface. In this embodiment, the insulated face is placed toward the structure, the exposed face radially outward. The primed numbers in FIG. 4 refer to parts and details corresponding to the parts and details designated by the respective unprimed numbers in FIG. 3.

Various changes and alterations will be apparent to those skilled in the art to the method provided by the present invention. It is intended that such changes and alterations, which do not depart from the spirit of the present invention, be included within the scope of the appended claims. The appended claims define the present invention; the foregoing description is employed for setting forth the present invention embodiments as being illustrative in nature.

I claim:

1. A method for cathodic protection monitoring of a metallic structure located in an earth region or in a body of water and subjected to cathodic protective currents from a remote anode electrode, comprising the steps of;
   (a) positioning a metallic specimen closely adjacent to but not in direct electrical contact with the structure and having exposed to the cathodic current a known surface area of at least one magnitude less than the structure, said metallic specimen being of like metallic material to said structure;
   (b) inducing current flow between the specimen and the structure until the potential difference between the specimen and the structure is substantially zero;
   (c) measuring the current flow between the specimen and the structure;
   (d) determining the current density impressed upon the specimen which current density is substantially identical to the current density impressed upon exposed like areas of the structure by cathodic current from the remote anode electrode; and
   (e) employing an anodic or cathodic induced current flow for varying the potential of the specimen relative to the structure to determine the anodic or cathodic reaction rate, respectively, the unprotected corrosion rate of the structure, and the cathodic current required to protect the structure.

2. The method of claim 1 wherein the specimen has a surface area substantially less than one-tenth the surface area of the structure receiving cathodic current from the remote anode.

3. The method of claim 1 wherein the initial potential of the specimen is varied to a second potential to induce anodic current flow from the specimen with the difference in potential between the initial potential and the second potential of the specimen being sufficient to determine the anodic reaction rate.

4. The method of claim 3 wherein the difference in potential is not in excess of about 1000 millivolts as the unprotected corrosion rate function.

5. The method of claim 1 wherein the initial potential of the specimen is varied to a second potential to induce cathodic current flow to the specimen with the difference in potential between the initial potential and the second potential of the specimen being sufficient to determine the cathodic reaction rate.

6. The method of claim 5 wherein the difference in potential in the linear polarization potential region is not in excess of about 400 millivolts as the unprotected corrosion rate function.

7. The method of claim 1 wherein the initial potential of the specimen is varied to a second potential to induce anodic current flow from the specimen with the difference in potential between the initial potential and the second potential of the specimen being sufficient to determine the anodic reaction rate and the initial potential of the specimen is varied to a second potential to induce cathodic current flow to the specimen with the difference in potential between the initial potential and the second potential of the specimen being sufficient to determine the cathodic reaction rate whereby correlation of anodic and cathodic currents to the difference in potentials provides information of the unprotected corrosion rate of the structure in the corrosive environment of the earth region or body of water.

8. The method of claim 7 wherein the difference in potential between the initial potential and the second potential by induced cathodic current flow is correlated whereby the cathodic polarization protective current is determined when the specimen is at zero potential difference relative to the structure.

9. The method of claim 1 wherein the steps (a) through (d) are repeated for a plurality of spaced apart specimens disposed along the structure whereby a current density profile of the cathodic current density provided by a plurality of remote anode electrodes is obtained.

10. The process of claim 1 wherein said remote anode electrode is a sacrificial anode.

11. The process of claim 1 wherein said remote anode electrode is an inert electrode and the cathodic current is provided by a d.c. source.

12. The process of claim 1 wherein the potential difference between said specimen and said structure is monitored by a zero resistance ammeter.

13. The process of claim 1 wherein the potential difference between said specimen and said structure is monitored by a variable conductance ammeter.

14. The process of claim 1 wherein the potential difference between said specimen and said structure is monitored by a dynamic analyzer.

15. The method of claim 1 wherein said metallic specimen is partially encased in an insulating covering.

16. The method of claim 1 wherein said structure is at least partially covered with or encased in a protective material.

17. The method of claim 16 wherein said protective material is bitumen or concrete.

18. A method for cathodic protection monitoring of a metallic structure located in an earth region or in a body of water and subjected to cathodic protective currents from a remote anode electrode, comprising the steps of:
   (a) positioning a metallic specimen closely adjacent to but not in direct electrical contact with the structure and having exposed to the cathodic current a known surface area of at least one magnitude less than the structure, said metallic specimen being of like metallic material to said structure;
   (b) inducing current flow between the specimen and the structure until the potential difference between the specimen and the structure is substantially zero;

(c) measuring the current flow between the specimen and the structure;
(d) determining the current density impressed upon the specimen which current density is substantially identical to the current density impressed upon exposed like areas of the structure by cathodic current from the remote anode electrode; and
(e) the potential difference between the specimen and structure being initially measured in the presence of cathodic current and then by the induced current required to bring said potential difference to zero.

19. The method of claim 18 wherein said metallic specimen is partially encased in an insulating covering.

20. The method of claim 18 wherein said structure is at least partially covered with or encased in a protective material.

21. The method of claim 20 wherein said protective material is bitumen or concrete.

* * * * *